United States Patent
Perl et al.

(10) Patent No.: US 12,378,387 B2
(45) Date of Patent: Aug. 5, 2025

(54) GLASS-FILLED PAEK MOULDING COMPOUNDS

(71) Applicant: Evonik Operations GmbH, Essen (DE)

(72) Inventors: Thomas Perl, Frankfurt am Main (DE); Jonas Scherble, Darmstadt (DE); Frank Claus, Essenheim (DE); Marc Knebel, Heddesheim (DE); Ingrid Velthoen, Beek (NL)

(73) Assignee: Evonik Operations Gmbh, Essen (DE)

( * ) Notice: Subject to any disclaimer, the term of this patent is extended or adjusted under 35 U.S.C. 154(b) by 558 days.

(21) Appl. No.: 17/771,426

(22) PCT Filed: Nov. 18, 2020

(86) PCT No.: PCT/EP2020/082521
§ 371 (c)(1),
(2) Date: Apr. 22, 2022

(87) PCT Pub. No.: WO2021/099379
PCT Pub. Date: May 27, 2021

(65) Prior Publication Data
US 2022/0403135 A1    Dec. 22, 2022

(30) Foreign Application Priority Data
Nov. 19, 2019 (EP) .................................... 19210076

(51) Int. Cl.
| *C08K 3/40* | (2006.01) |
| *A61L 27/44* | (2006.01) |
| *C08K 3/22* | (2006.01) |
| *C08K 3/30* | (2006.01) |

(52) U.S. Cl.
CPC .................. *C08K 3/40* (2013.01); *C08K 3/22* (2013.01); *C08K 3/30* (2013.01); *A61L 27/446* (2013.01); *A61L 2430/12* (2013.01); *C08K 2003/2241* (2013.01); *C08K 2003/2251* (2013.01); *C08K 2003/3045* (2013.01); *C08K 2201/005* (2013.01); *C08K 2201/014* (2013.01)

(58) Field of Classification Search
CPC ... C08K 3/40; C08K 3/22; C08K 3/30; C08K 2003/2241; C08K 2003/2251; C08K 2003/3045; C08K 2201/005; C08K 2201/019; A61L 27/446; A61L 2430/12; A61L 27/10; A61L 27/18; C08L 71/00
See application file for complete search history.

(56) References Cited

U.S. PATENT DOCUMENTS

| 5,874,176 | A | 2/1999 | Kamei et al. |
| 9,567,444 | B2 | 2/2017 | Neuhaeuser et al. |
| 2005/0244773 | A1 | 11/2005 | Abels et al. |
| 2013/0012643 | A1 | 1/2013 | Monsheimer et al. |
| 2013/0216827 | A1 | 8/2013 | Parusel et al. |
| 2015/0011673 | A1 | 1/2015 | Yamagawa et al. |
| 2015/0099821 | A1* | 4/2015 | Lu .......................... A61K 6/887 522/48 |
| 2017/0044348 | A1* | 2/2017 | Yamagawa ............. C08L 71/10 |
| 2019/0282455 | A1 | 9/2019 | Shimizu et al. |
| 2020/0108174 | A1 | 4/2020 | Prabhu et al. |
| 2021/0008252 | A1 | 1/2021 | Prabhu et al. |
| 2021/0046218 | A1 | 2/2021 | Prabhu et al. |

FOREIGN PATENT DOCUMENTS

| CN | 102863784 A | 1/2013 |
| CN | 103483768 A | 1/2013 |
| EP | 0 683 210 A2 | 11/1995 |
| EP | 3 141 581 A1 | 3/2017 |
| JP | 6013217 * | 8/2014 |
| JP | 6013217 B2 | 10/2016 |
| JP | 2018-95694 | 6/2018 |
| WO | 2006/094690 A1 | 9/2006 |

OTHER PUBLICATIONS

English International Search Report mailed on Feb. 10, 2021 in PCT/EP2020/082521 (2 pages).
German International Search Report mailed on Feb. 10, 2021 in PCT/EP2020/082521 (3 pages).
German Written Opinion mailed on Feb. 10, 2021 in PCT/EP2020/082521 (6 pages).

* cited by examiner

*Primary Examiner* — Katarzyna I Kolb
(74) *Attorney, Agent, or Firm* — Grüneberg and Myers PLLC

(57) ABSTRACT

The present invention is directed to moulding compounds comprising polyarylene ether ketones and glass particles, with the glass particles being broken, irregularly shaped particles.

21 Claims, No Drawings

GLASS-FILLED PAEK MOULDING COMPOUNDS

CROSS REFERENCE TO RELATED APPLICATIONS

This application is a 35 U.S.C. § 371 U.S. national phase entry of International Application No. PCT/EP2020/082521 having an international filing date of Nov. 18, 2020, which claims the benefit of European Application No. 19210076.6 filed Nov. 19, 2019, each of which is incorporated herein by reference in its entirety.

FIELD

The present invention is directed to moulding compounds comprising polyarylene ether ketones and glass particles, with the glass particles being broken, irregularly shaped particles.

BACKGROUND

Polyarylene ether ketones (PAEK) are naturally slightly grey in color and not very suitable for aesthetic uses. Because of this, a certain amount of dye (for example titanium dioxide to achieve a white color) is added to the raw material, for example by means of compounding. The material is available either in the form of granules for injection moulding or as semifinished product (extruded solid rods) for machining.

For use of the material in dentistry, for example in bridgework, the PEEK currently available on the market is unsuitable for use in multi-unit bridgework, since it would sag—in other words, it is not "solid" enough, i.e. the tensile modulus of the material is insufficiently high. The tensile modulus of the available variants is approx. 3500 MPa (unfilled) to 4100 MPa (colored material).

Common materials for increasing the tensile modulus in PEEK are fibers, for example carbon fibers or glass fibers, as disclosed in WO 2006/094690. This is already being employed commercially in industry. The tensile modulus can indeed be increased significantly by this. However, a disadvantage is that the material no longer behaves homogeneously and becomes anisotropic. It can absorb a lot of force in a particular direction (in the direction of the fibers), but even slight changes in angle relative to the direction of the fibers are enough to cause a dramatic decrease in tensile modulus. A further disadvantage for the medical sector is that the fibers need to be biocompatible, whereas fiber ends that are not encapsulated in the material may cause irritation, for example of mucous membranes.

SUMMARY

To meet the requirements of a material for uses such as multi-unit bridgework in dentistry, a reinforced material would need to be developed. A tensile modulus of more than 5500 MPa should be the aim here. PEEK can in principle be reinforced through the addition of fillers. Added dye particles reinforce the polymer matrix. The strength (expressed as tensile modulus according to EN ISO 527) is known to increase with the amount of filler added. On the other hand, the addition of a filler reduces the ductility of the material. This means that the material becomes more brittle when fillers are added and consequently breaks more readily when subjected to stress. The tensile modulus could be increased by the desired degree through simple addition of, for example, titanium dioxide. However, since the material would then be too brittle, this offers no solution.

The object is to find a particulate filler or a mixture of fillers that not only increases the tensile modulus, but maintains the ductility of the material as far as possible.

The object was achieved by using certain glass particles.

DETAILED DESCRIPTION

The invention relates to a moulding compound that comprises at least 30% by weight of polyarylene ether ketone (PAEK), preferably 30% to 80% by weight, more preferably 40% to 70% by weight, particularly preferably 50% to 60% by weight, based on the total moulding compound, and at least two fillers, wherein one of the fillers consists of glass particles, with the glass particles having a particle size distribution $d_{50}$ in accordance with ISO 13320:2009 of 0.1 µm to 10 µm.

The invention further provides shaped bodies comprising the moulding compounds according to the invention.

The invention further provides for the use as a support element of the shaped bodies according to the invention.

The moulding compounds according to the invention, shaped bodies comprising the moulding compounds of the invention and use according to the invention are described hereinafter by means of illustrative examples, without any intention that the invention be restricted to these illustrative embodiments. Where ranges, general formulae, or classes of compound are stated below, these are intended to comprise not only the corresponding ranges or groups of compounds explicitly mentioned, but also all subranges and subgroups of compounds that can be obtained by extracting individual values (ranges) or compounds. Where documents are cited within the context of the present description, the entire content thereof is intended to be part of the disclosure content of the present invention. Where percentage values are given hereinafter, these are values in % by weight unless otherwise stated. In the case of compositions, the percentage figures are based on the entire composition unless otherwise stated. Where average values are given hereinafter, these are mass averages (weight averages) unless stated otherwise. Where measured values are given hereinafter, these measured values were determined at a pressure of 101 325 Pa and at a temperature of 25° C. unless stated otherwise.

The scope of protection includes finished and packaged forms of the products according to the invention that are customary in commerce. The product as such is covered, as are possible comminuted forms (for example ground materials, crude forms for extrusion such as granules, wires, rods, etc.) insofar as these are not defined in the claims.

An advantage of the moulding compounds according to the invention is that the glass particles are dispersed homogeneously in the polymer matrix. A further advantage is that this homogeneous dispersion is effected without addition of a dispersant.

An advantage of the shaped bodies according to the invention is that the elongation at break and Charpy notched impact strength for the same filler content (% by weight) are higher than that of shaped bodies produced from moulding compounds comprising prior-art fillers such as titanium dioxide or fumed silica without glass particles.

Polyarylene ether ketones (PAEK) are preferably selected from polyether ether ketone (PEEK), polyether ketone (PEK), polyether diphenyl ether ketone (PEDEK), polyether ketone ether ketone ketone (PEKEKK), polyether ketone ketone (PEKK), and mixtures and copolymers thereof. More preferred aromatic polyethers are polyether ether ketone (PEEK), polyether ketone (PEK), polyether diphenyl ether ketone (PEDEK), polyether ketone ether ketone ketone (PEKEKK), polyether ketone ketone (PEKK); even more preferred are polyether ether ketone (PEEK) and polyether diphenyl ether ketone (PEDEK).

In the case of copolymers, the various units of polyarylene ether ketone (PAEK) show a statistical distribution. Statistical distributions are of blockwise construction with any desired number of blocks and with any desired sequence or they are subject to a randomized distribution; they may also have an alternating construction or else form a gradient over the polymer chain; in particular they can also form any mixed forms in which groups with different distributions may optionally follow one another. Specific embodiments may result in statistical distributions being restricted as a consequence of the embodiment. For all regions unaffected by such restriction, the statistical distribution is unchanged.

The polyarylene ether ketones (PAEK) further preferably have the following units:

-Ph-CO-Ph-O-Ph-O—*, where Ph are phenyl radicals and the asterisks denote other constituents of the polymer chain.

The polyarylene ether ketones (PAEK) further more preferably have units of the formula (I)

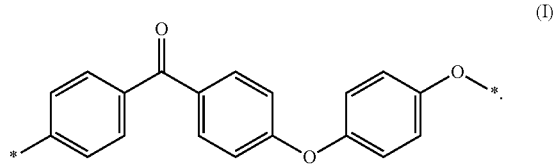

(I)

Particular preference as the polyarylene ether ketone (PAEK) is given to a polyether ether ketone (PEEK).

The glass particles are solid, broken and irregularly shaped particles.

The glass is an inorganic glass, preferably comprising silicate, borate and aluminate as crosslinking units. In product specifications, silicate is specified and calculated as $SiO_2$, borate as $B_2O_3$ and aluminate as $Al_2O_3$. More preferably, silicates form the majority of the crosslinking units. Glasses of this type are known to those skilled in the art as aluminoborosilicate glasses. Further preferably, the $SiO_2$ content is equal to or greater than 35% by weight, more preferably greater than 45% by weight and particularly preferably equal to or greater than 50% by weight, based on the total mass of the glass, and the $SiO_2$ content is preferably equal to or less than 95% by weight, 85% by weight, 80% by weight and particularly preferably less than or equal to 75% by weight. Preferably, the content of phosphate-based crosslinking units (specified and calculated as $P_2O_5$) is less than 5% by weight, preferably less than 2% by weight, based on the content in the glass, and in particular the glass does not contain any phosphate.

Particular preference is given to glasses that contain
35% to 85% by weight, 40% to 75% by weight, preferably 45% to 55% by weight, of $SiO_2$, 5% to 20% by weight, preferably 9% to 16% by weight, of $B_2O_3$,
0.5% to 20% by weight, 1% to 19% by weight, 5% to 18% by weight, preferably 9% to 16% by weight, of $Al_2O_3$,
0% to 10% by weight of $K_2O$ and
up to 40% by weight, preferably 5% to 30% by weight, in particular 10% to 20% by weight, of at least one metal oxide, with the percentages being based on the total mass of the glass; the content of impurities such as compounds of lead, cadmium, mercury and hexavalent chromium is not more than 100 ppm and is disregarded. These metal oxides can confer upon the glass a certain opacity to X-rays. Suitable metal oxides may be selected from BaO, SrO, $Cs_2O$, $SnO_2$.

The glass contains $SiO_2$ as glass-forming component in a proportion of 35% to 85% by weight. In advantageous embodiments, the upper limit for $SiO_2$ can be set at 73% by weight, preferably 70% by weight, more preferably 68.5% by weight. The lower limit according to the invention is 35% by weight. Lower contents can adversely affect chemical resistance.

Impurities generally do not exceed a proportion of 0.2% by weight, in particular 0.1% by weight. This of course also encompasses the complete absence of the respective component. "Free of a component" thus means that this component is essentially absent in this glass, i.e. that such a component is present at most as an impurity in the glass, but is not added to the glass composition as an individual component.

Contamination of the glass with undesirable substances should generally not exceed 300 ppm for $Fe_2O_3$, preferably not more than 100 ppm, 30 ppm for PbO, 20 ppm for $As_2O_3$, 20 ppm for $Sb_2O_3$ and 100 ppm for other impurities.

It is envisaged that the glass according to the invention is optionally free of $CeO_2$ and $TiO_2$ except for at most impurities. Because of their absorbance in the UV range, $CeO_2$ and $TiO_2$ shift the UV edge of the glass, which can result in an undesirable yellowish color. In a preferred embodiment, the glass according to the invention is free of $TiO_2$. A particularly preferred embodiment of the glass is free of $TiO_2$ and $ZrO_2$.

It is of course also possible to tailor the color appearance of the glass for optics or other technical uses by adding oxides customary for this purpose. Oxides suitable for coloring glasses are known to those skilled in the art; examples include CuO and CoO, which can be added for such purposes in a content of preferably >0% to 0.5% by weight.

In addition, the glass can be conferred with antiseptic properties through the addition of, for example, $Ag_2O$ in a content of >0% to 3% by weight. Alkali metal oxides from the group $Li_2O$, $Na_2O$, $K_2O$ may be necessary in order to able to melt the glass at all. $K_2O$ is used to adjust the melting temperature and at the same time strengthens the glass network. It is therefore according to the invention present in the glass composition in a proportion of 0% to 10% by weight. The range is preferably from 0% to 7% by weight, more preferably from 0% to 5% by weight. The upper limit of 10% by weight according to the invention should not be exceeded, because the content of alkali oxides reduces chemical resistance. An upper limit of 7% by weight, preferably 5% by weight, more preferably 4% by weight can also advantageously be chosen.

The small size of sodium and lithium ions means that they can leach more easily from the glass matrix, which can reduce chemical resistance, particularly hydrolytic resistance. Preferably, the total content of the oxides $K_2O$, $Na_2O$ and $Li_2O$ is not more than 6% by weight, preferably not more than 5% by weight, more preferably not more than 4% by weight. In an advantageous embodiment of the invention, the glass is free of $Li_2O$ except for at most impurities. In an even more preferred embodiment, the glass is free of $Na_2O$ and $Li_2O$.

The glass particles are preferably solid. "Solid" in the context of the invention means that, apart from glass, the particles contain not more than 10% by volume, preferably not more than 5% by volume, more preferably not more than 2% by volume, especially preferably not more than 1% by volume, of gaseous inclusions and particularly preferably contain none at all. The term "solid" preferably excludes hollow bodies such as hollow glass beads or bubbles.

The glass particles are preferably broken. "Broken" in the context of the invention means that the particles are products obtained from crushing processes, such as preferably ground materials. The glass particles are preferably irregularly shaped. The particles are preferably not so-called spherical particles, for example spheres or ellipsoids. The particles are preferably also not fiber materials.

More preferably, the glass particles are solid and broken, and irregularly shaped.

The glasses preferably have a refractive index of 1.48 to 1.56. The refractive index is determined in a known manner, preferably on an unbroken body.

Particular preference is given to so-called dental glasses.

The moulding compounds according to the invention preferably contain not more than 5% by weight, not more than 3% by weight, not more than 2% by weight, not more than 1% by weight, of glass particles of any shape that are outside the specifications mentioned herein and particularly preferably none at all.

All percentages by weight specified for glasses are in each case based on the content in the glass.

In a preferred embodiment, the surface of the glass powder, i.e. the surface of the glass powder particles, is silanized using customary methods. Silanization can improve the binding of inorganic fillers to the plastic matrix.

The glass particles have a particle size distribution $d_{50}$ in accordance with ISO 13320:2009 from 0.1 µm to 10 µm, preferably from 0.4 to 2 µm, in particular from 0.5 to 1.2 µm.

The glass particles are preferably free of particles having a particle size of greater than 50 µm, more preferably of greater than 40 µm, even more preferably 30 µm, especially preferably 20 µm, more especially preferably 15 µm and particularly preferably free of particles having a particle size greater than 10 µm. The $d_{99}$ values of the glass particles are preferably less than or equal to four times the $d_{50}$ value.

The moulding compound according to the invention preferably contains 10 to 50% by weight of glass particles based on the total moulding compound.

The moulding compound according to the invention preferably comprises further fillers. The moulding compound according to the invention preferably contains 10% to 60% by weight of fillers, more preferably 20% to 55% by weight, 30% to 50% by weight and 40% to 45% by weight, based on the total moulding compound.

Preferred fillers are $TiO_2$ and $BaSO_4$.

These further fillers constitute dyes and therefore do not contain any particles smaller than 100 nm.

The measurement of the particle size distribution is carried out in accordance with ISO 13320 with dry-dispersed particles.

The particle sizes are preferably determined in accordance with ISO 13320 with a Malvern Mastersizer 3000 in a stream of dry air.

The moulding compound according to the invention preferably contains not less than 50% by weight of glass particles, preferably not less than 55% by weight, 60% by weight, 65% by weight, 70% by weight and more preferably not less than 75% by weight, based on the total mass of the fillers.

The matrix of the moulding compound according to the invention, i.e. the proportion of the moulding compound minus fillers, contains 80% to 100% by weight, preferably 85% to 99% by weight, more preferably 90% to 95% by weight and particularly preferably 90% to 92% by weight, of polyaryl ether ketone (PAEK), based on the total mass of the polymer matrix.

In addition to the polyarylene ether ketone (PAEK), further components may be present in the matrix:
- 0% to 5% by weight of X-ray contrast medium, preferably 0.1% to 4% by weight, $BaSO_4$ excepted, which is a filler,
- 0% to 10% by weight of dyes, preferably 0.1% to 5% by weight, more preferably 0.2% to 3% by weight, in particular 0.3% to 1% by weight, $TiO_2$ excepted, which is a filler,
- 0% to 5% by weight of impact modifier, preferably 0.1% to 2% by weight,
- 0% to 10% by weight of other polymers,
- 0% to 10% of other additives, based on the polymer matrix.

The other polymers are preferably not polyphenyl sulfones (PPSU), polysulfones (PSU), fluoropolymers, polyamides (PA), polyacrylates (such as for example polymethyl methacrylates (PMMA)), polyesters, polyurethanes, polyoxymethylene (POM) and acetal polymers.

More preferably, the moulding compounds according to the invention do not contain polyphenyl sulfones (PPSU), polysulfones (PSU), fluoropolymers, polyamides (PA), polyacrylates (such as for example polymethyl methacrylates (PMMA)), polyesters, polyurethanes, polyoxymethylene (POM) and acetal polymers.

X-ray contrast media may be any substances that are approved for use in humans and animals and that cause a corresponding shadow in the X-ray image. Preferred substances are barium oxide, strontium sulfate and/or strontium oxide.

Dyes may be any substances approved for use in humans and animals that guarantee appropriate coloring.

Preferred colorants are inorganic pigments, preferably metal oxides. Particular preference is given to iron oxides as red pigment and rutile pigments for other colors, for example chromium titanium yellow and nickel titanium yellow as yellow pigments. Metal oxides that have already been claimed as fillers are not to be counted as inorganic pigments.

In addition, the moulding compounds according to the invention contain no fiber materials based on the total moulding compound at all. Fiber materials are characterized in that they have an aspect ratio of greater than 5, more preferably greater than 3. The aspect ratio is known to those skilled in the art as the ratio of the largest dimension and the smallest dimension. Fiber materials include glass fibers or carbon fibers, including so-called carbon nanotubes.

The moulding compounds according to the invention preferably comprise PEEK, 10% to 60% by weight of fillers, based on the total moulding compound, and not less than 50% by weight of glass particles, preferably not less than 55% by weight, 60% by weight, 65% by weight, 70% by weight and more preferably not less than 75% by weight, based on the total amount of fillers.

The moulding compounds according to the invention more preferably comprise PEEK, $TiO_2$ as filler and not less than 50% by weight of glass particles, preferably not less than 55% by weight, 60% by weight, 65% by weight, 70% by weight and more preferably not less than 75% by weight, based on the total amount of fillers.

The moulding compounds according to the invention even more preferably comprise PEEK, $TiO_2$ as filler and not less than 60% by weight of glass particles, wherein the glass of the glass particles comprises silicate, borate and aluminate crosslinking units (specified and calculated as $SiO_2$, $B_2O_3$ $Al_2O_3$) and preferably a content of phosphate-based crosslinking units (specified and calculated as $P_2O_5$) of less than 5% by weight, preferably less than 2% by weight, based on the content in the glass, and in particular the glass contains no phosphate at all.

The moulding compounds according to the invention likewise even more preferably comprise PEEK, $TiO_2$ as filler and not less than 50% by weight of glass particles, wherein the glass of the glass particles comprises silicate, borate and aluminate crosslinking units (specified and calculated as $SiO_2$, $B_2O_3$ $Al_2O_3$) and preferably a content of phosphate-based crosslinking units (specified and calculated as $P_2O_5$) of less than 2% by weight, based on the content in the glass, and the glass particles have a particle size distribution $d_{50}$ in accordance with ISO 13320:2009 from 0.4 to 2 in particular from 0.5 to 1.2 μm.

The moulding compounds according to the invention particularly preferably comprise PEEK, $TiO_2$ as filler and not less than 50% by weight of glass particles, wherein the glass of the glass particles comprises silicate, borate and aluminate crosslinking units (specified and calculated as $SiO_2$, $B_2O_3$ $Al_2O_3$) and preferably a content of phosphate-based crosslinking units (specified and calculated as $P_2O_5$) of less than 2% by weight, based on the content in the glass, and in particular the glass contains no phosphate at all, wherein the moulding compound contains no fiber materials based on the total moulding compound at all.

The invention further provides for the use of the moulding compound according to the invention for production of medical devices, preferably implantable bone prostheses or as dental prostheses.

The moulding compound according to the invention is produced from the individual constituents preferably by melt mixing in a kneading unit, i.e. with employment of shear forces.

The moulding compounds of the invention may comprise further additives.

Preferred additives are oxidation stabilizers, UV stabilizers, hydrolysis stabilizers, impact modifiers, pigments, dyes and/or processing aids.

In a preferred embodiment, the moulding compounds comprise an effective amount of an oxidation stabilizer and more preferably an effective amount of an oxidation stabilizer in combination with the effective amount of a copper-containing stabilizer. Examples of suitable oxidation stabilizers include aromatic amines, sterically hindered phenols, phosphites, phosphonites, thiosynergists, hydroxylamines, benzofuranone derivatives, acryloyl-modified phenols etc. A great many types of such oxidation stabilizers are commercially available, for example under the trade names Naugard 445, Irganox 1010, Irganox 1098, Irgafos 168, P-EPQ or Lowinox DSTDP. In general, the moulding compounds contain about 0.01% to about 2% by weight and preferably about 0.1% to about 1.5% by weight of an oxidation stabilizer.

In addition, the moulding compounds may also comprise a UV stabilizer or a light stabilizer of the HALS type. Suitable UV stabilizers are primarily organic UV absorbers, for example benzophenone derivatives, benzotriazole derivatives, oxalanilides or phenyltriazines. Light stabilizers of the HALS type are tetramethylpiperidine derivatives; these are inhibitors that act as radical scavengers. UV stabilizers and light stabilizers may advantageously be used in combination. A great many types of both are commercially available; the manufacturer's instructions can be followed in respect of the dosage.

The moulding compounds may additionally comprise a hydrolysis stabilizer, for instance a monomeric, oligomeric or polymeric carbodiimide or a bisoxazoline.

The moulding compounds may further comprise impact modifiers. Impact-modifying rubbers for polyamide moulding compounds form part of the prior art. They contain functional groups which originate from unsaturated functional compounds that have been either included in the main chain polymer or grafted onto the main chain. The most commonly used are EPM or EPDM rubber that has been free-radically grafted with maleic anhydride. Rubbers of this kind can also be used together with an unfunctionalized polyolefin, for example isotactic polypropylene, as described in EP0683210A2 (U.S. Pat. No. 5,874,176A).

Examples of suitable processing aids include paraffins, fatty alcohols, fatty acid amides, stearates such as calcium stearate, paraffin waxes, montanates or polysiloxanes.

Shaped bodies according to the invention are preferably semifinished products produced by extrusion. These semifinished products are preferably solid blanks, for example so-called milling blanks, from which the shaped pieces, for example prostheses, are subsequently produced through machining.

Further shaped bodies according to the invention include at least a layer produced from the moulding compounds according to the invention, wherein the layer may also be a partial shaped body.

The shaped bodies are preferably produced entirely from the moulding compounds according to the invention.

Preferably, in accordance with DIN EN 527-2, 2012 the shaped bodies according to the invention have a tensile modulus of greater than 5500 MPa.

Further preferably, in accordance with DIN EN 527-2, 2012 the shaped bodies according to the invention have a tensile modulus of greater than 4300 MPa and an elongation at break of more than 15%.

Even more preferably, in accordance with DIN EN 527-2, 2012 the shaped bodies according to the invention have a tensile modulus of greater than 4300 MPa, preferably from 4300 to 5300 MPa, and a value X of greater than 100, preferably greater than 150. An upper limit for the value X can be 500.

The value X is defined as the value obtained by multiplying the elongation at break (measured in %) in accordance with DIN EN 527-2, 2012 and the Charpy notched impact strength (measured in $kJ/m^2$) in accordance with DIN 179.

Particularly preferably, in accordance with DIN EN 527-2, 2012 the shaped bodies according to the invention have a tensile modulus of greater than 5500 MPa and a value X of greater than 30.

The shaped body according to the invention is preferably a dental prosthesis. Prostheses are partial or full dentures, crowns and bridges. The teeth and the connecting bridge can be made here from different materials, but preferably from one or more moulding compounds according to the invention, that differ, for example, in their color.

The mechanical tests are known to those skilled in the art and are preferably carried out in accordance with DIN EN 527-2, 2012. Testing is preferably carried out using so-called dumbbell specimens of type 1BA. Notched impact strength tests are preferably carried out according to ISO 180 or ISO 179.

In the examples, the following components and moulding compounds were used. Vestakeep is a trademark of Evonik, Germany and refers to moulding compounds based on polyether ether ketone with and without additives:

Vestakeep® Dental DC4420 G, a white-colored PEEK moulding compound for use in dentistry, Vestakeep® Dental DC4450 G, a yellow-colored PEEK moulding compound for use in dentistry, and Vestakeep® Dental D4 G were used.

Glasses of varying composition and different particle sizes were tested.

| Glass type 1 | $SiO_2$ | approx. 50% by weight |
|---|---|---|
| | SrO | approx. 20% by weight |
| | $B_2O_3$ | approx. 15% by weight |
| | $Al_2O_3$ | approx. 15% by weight |
| | BaO | approx. 1% by weight |
| Glass type 2 | $SiO_2$ | approx. 55% by weight |
| | BaO | approx. 25% by weight |
| | $B_2O_3$ | approx. 10% by weight |
| | $Al_2O_3$ | approx. 10% by weight |

Glass 1 was used with the particle sizes a)=0.4 μm, b)=0.8 μm and c)=1.0 μm; glass 2 with a)=0.4 μm, b)=0.7 μm and c)=1.0 μm and d) 3.0 μm.

The particle sizes are $d_{50}$ values. The particle sizes of the glasses were determined by laser diffraction with a Cilas 1064L in accordance with ISO 13320: 2009.

$TiO_2$ Titanium dioxide
Yellow pigment Chromium titanium yellow
$BaSO_4$ Barium sulfate;
Moulding compounds A having varying contents of fillers.

TABLE 1

Composition of the moulding compounds A of example 1.

| Moulding compound A | $TiO_2$ [wt.-%] | $BaSO_4$ [wt.-%] | yellow | Total filler content [wt.-%] | Glass content [wt.-%] |
|---|---|---|---|---|---|
| 1 | 25.2 | 5.81 | 1.26 | 32.27 | 0 |
| 2 | 29.73 | 5.58 | 1.49 | 36.8 | 0 |
| 3 | 38.1 | 5.14 | 1.9 | 45.14 | 0 |
| 4 | 41.81 | 4.95 | 2.09 | 48.85 | 0 |
| 5 | 45.25 | 4.77 | 2.26 | 52.28 | 0 |
| 6 | 48.46 | 4.6 | 2.42 | 55.48 | 0 |
| 7 | 51.45 | 4.45 | 2.57 | 58.47 | 0 |
| 8 | 10 | 0 | 0 | 20 | 50 |
| 9 | 5 | 0 | 0 | 20 | 75 |
| 10 | 0 | 0 | 0 | 20 | 100 |
| 11 | 10 | 0 | 0 | 25 | 60 |
| 12 | 5 | 0 | 0 | 25 | 80 |
| 13 | 5 | 0 | 0 | 30 | 83.33 |

TABLE 2

Composition of the moulding compounds B of example 1. The amounts were 10.48% by weight of $TiO_2$ and 0.52% by weight of chromium titanium yellow.

| Moulding compound B | Glass (type; size) [wt.-%] | Total filler content [wt.-%] | Glass content [wt.-%] |
|---|---|---|---|
| 14 | 30 (1; 1 μm) | 41 | 73.17 |
| 15 | 30 (1; 0.7 μm) | 41 | 73.17 |
| 16 | 30 (1; 0.4 μm) | 41 | 73.17 |
| 17 | 28.5 (2; 3 μm) | 39.5 | 72.15 |
| 18 | 28.5 (2; 1 μm) | 39.5 | 72.15 |
| 19 | 28.5 (2; 0.7 μm) | 39.5 | 72.15 |
| 20 | 28.5 (2; 0.4 μm) | 39.5 | 72.15 |

Example 2, Mechanical Tests:

The measured values shown in tables 3 (in accordance with DIN EN ISO 527-2, 2012) (Charpy notched impact strength, abbreviated to Charpy in accordance with DIN 179) are arithmetic mean values for 5 shaped units (tensile tests) and 10 shaped units (impact test). The designation of the test specimens was taken from the designation of the moulding compounds.

TABLE 3a

Determination of mechanical properties according to example 2; nd means that the value was not determined.

| Test specimen A | Tensile modulus [MPa] | Charpy | Elongation at break [%] | Value X |
|---|---|---|---|---|
| 1 | 4899 | 6.7 | 11.3 | 76 |
| 2 | 5261 | 6.8 | 9.5 | 65 |
| 3 | 5932 | 5 | 6.5 | 33 |
| 4 | 6468 | 4.7 | 4.2 | 20 |
| 5 | 6963 | 4.4 | 3.4 | 15 |
| 6 | 7453 | 4.2 | 2.4 | 10 |
| 7 | 8258 | 3.5 | 2 | 7 |
| 8 | 4414 | 8.8 | 26 | 229 |
| 9 | 4552 | 9.2 | 17.7 | 163 |
| 10 | 4635 | 8.8 | 24.8 | 218 |
| 11 | 4737 | 9.7 | 21.7 | 210 |
| 12 | 4855 | 10.8 | 20.5 | 221 |
| 13 | 5237 | 11.6 | 18.2 | 211 |

The results show that dental glass has a beneficial effect on the mechanical properties of the shaped bodies. It stiffens the material to the same extent (tensile modulus) as $TiO_2$ filler materials, but with preservation of comparatively higher elongation at break values.

TABLE 3b

Results of test series 3

| Test specimen B | Tensile modulus [MPa] | Charpy | Elongation at break [%] | Value X |
|---|---|---|---|---|
| 14 | 6085 | 8.1 | 9.1 | 74 |
| 15 | 5952 | 10.3 | 8.9 | 92 |
| 16 | 5989 | 8.3 | 7.4 | 61 |
| 17 | 5953 | 3.4 | 5.6 | 19 |
| 18 | 6078 | 4.5 | 9.2 | 41 |
| 19 | 5996 | 7 | 7.5 | 53 |
| 20 | 5731 | 6.5 | 8 | 52 |

The invention claimed is:

1. A moulding compound comprising at least 30% by weight of polyarylene ether ketone (PAEK), based on the total moulding compound, and at least two fillers,
    wherein one of the fillers consists of glass particles, with the glass particles having a
    particle size distribution $d_{50}$ in accordance with ISO 13320:2009 of 0.1 μm to 10 μm,
    wherein the glass of the glass particles is an inorganic glass comprising silicate, borate and aluminate cross-linking units, specified and calculated as $SiO_2$, $B_2O_3$, $Al_2O_3$,
    wherein the at least one further filler does not contain any particles under 100 nm, determined in accordance ISO 13320,
    wherein the moulding compound contains no fiber materials at all; and
    wherein the glass has a content of phosphate-based crosslinking units (specified and calculated as $P_2O_5$) of more than 0% and less than 5% by weight, based on the content in the glass.

2. The moulding compound according to claim 1, wherein the glass comprises a total of not more than 6% by weight, of $K_2O$, $Na_2O$ and $Li_2O$, based on the content in the glass.

3. The moulding compound according to claim 1, wherein the glass particles are solid and broken, and irregularly shaped.

4. The moulding compound according to claim 1, wherein the glass particles have a particle size distribution $d_{50}$ in accordance with ISO 13320:2009 from 0.4 to 2 μm.

5. The moulding compound according to claim 1, wherein the moulding compound contains from 10% to 60% by weight of fillers, based on the total moulding compound.

6. The moulding compound according to claim 1, wherein the moulding compound contains not less than 50% by weight of glass particles, based on the total mass of the fillers.

7. A shaped body comprising the moulding compound according to claim 1.

8. A medical device of the shaped body according to claim 7.

9. The moulding compound according to claim 1, wherein the glass has a content of phosphate-based crosslinking units (specified and calculated as $P_2O_5$) of more than 0% and less than 2% by weight based on the content in the glass.

10. The moulding compound according to claim 1, wherein the glass comprises a total of not more than 5% by weight of $K_2O$, $Na_2O$ and $Li_2O$, based on the content in the glass.

11. The moulding compound according to claim 1, wherein the glass comprises a total of not more than 4% by weight of $K_2O$, $Na_2O$ and $Li_2O$, based on the content in the glass.

12. The moulding compound according to claim 1, wherein the moulding compound contains from 20% to 55% by weight of fillers, based on the total moulding compound.

13. The moulding compound according to claim 1, wherein the moulding compound contains from 30% to 50% by weight of fillers, based on the total moulding compound.

14. The moulding compound according to claim 1, wherein the moulding compound contains from 40% to 45% by weight of fillers, based on the total moulding compound.

15. The moulding compound according to claim 1, wherein the moulding compound contains not less than 55% by weight of glass particles, based on the total mass of the fillers.

16. The moulding compound according to claim 1, wherein the moulding compound contains not less than 60% by weight of glass particles, based on the total mass of the fillers.

17. The moulding compound according to claim 1, wherein the moulding compound contains not less than 65% by weight of glass particles, based on the total mass of the fillers.

18. The moulding compound according to claim 1, wherein the moulding compound contains not less than 70% by weight of glass particles, based on the total mass of the fillers.

19. The moulding compound according to claim 1, wherein the moulding compound contains not less than 75% by weight of glass particles, based on the total mass of the fillers.

20. The moulding compound according to claim 1, wherein the glass particles have a particle size distribution $d_{50}$ in accordance with ISO 13320:2009 from 0.5 to 1.2 μm.

21. The shaped body according to claim 7, having a tensile modulus of greater than 5500 MPa, and/or an elongation at break of more than 15%.

* * * * *